United States Patent [19]

Inouye et al.

[11] Patent Number: 4,563,472

[45] Date of Patent: Jan. 7, 1986

[54] IODOALLYL AND IODOPROPARGYL SUBSTITUTED TETRAZOLES AND ANTI-MICROBIAL COMPOSITIONS THEREOF

[75] Inventors: Shigeharu Inouye; Taro Niida; Keinosuke Miyauchi, all of Yokohama; Kuniomi Matsumoto, Tokyo; Eiichi Akita; Masao Koyama, both of Yokohama; Fumio Kai, Fujisawa; Takashi Tsuruoka, Kawasaki, all of Japan

[73] Assignee: Meiji Seika Kaisha, Ltd., Tokyo, Japan

[21] Appl. No.: 433,011

[22] Filed: Oct. 6, 1982

[51] Int. Cl.$^4$ .................. A61K 31/41; C07D 257/04
[52] U.S. Cl. ..................................... 514/381; 548/250
[58] Field of Search ............ 548/250; 424/269; 514/381

[56] References Cited

FOREIGN PATENT DOCUMENTS 0062159  4/1983  Japan ..................... 548/561

Primary Examiner—Glennon H. Hollrah
Assistant Examiner—D. B. Springer
Attorney, Agent, or Firm—James J. Ralabate

[57] ABSTRACT

Triiodoallyl- or iodopropargyl-substituted heterocyclic aromatic compounds which can be prepared by reacting unsubstituted- or substituted nitrogen-containing heterocyclic compounds with corresponding iodine containing alcohol reactive derivatives in the presence of a base in an inert organic solvent. These new heterocyclic aromatic compounds have remarkable antibacterial and antifungal activities and are useful as antibacterial and antifungal agents in medicinal, agricultural and industrial fields.

14 Claims, No Drawings

IODOALLYL AND IODOPROPARGYL SUBSTITUTED TETRAZOLES AND ANTI-MICROBIAL COMPOSITIONS THEREOF

DETAILED DESCRIPTION OF THE INVENTION

This invention relates to a compound having the formula (I)

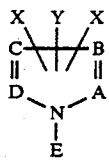

wherein E is a 2,3,3-triiodoallyl group or a 3-iodopropargyl group; A, B, C and D are individually a nitrogen atom or a carbon atom provided that all of A, B, C and D do not represent nitrogen atoms; and X, Y and Z may be the same or different and represent a hydrogen atom, a chlorine atom, a nitro group, a phenyl group, a 3-chloro-2-nitrophenyl group, a methyl group, a methoxycarbonyl group or an ethoxycarbonyl group, said atom or group being attached to a carbon atom of A, B, C or D, as well as an antimicrobial and antifungal composition which comprises as an active ingredient at least one of the compound (I).

The present inventors previously found a new antibiotic substance SF-2080A (also called pyrrolomycin A) and filed a Japanese Patent Application No. 141123/1980 disclosing and claiming the said antibiotic substance, a process for producing the same and an antifungal composition containing as an active ingredient the said antibiotic substance (See, Japanese Patent Laid-Open Application No. 90099/1981).

Since then, the present inventors have made structural modification of pyrrolomycin A by chemical reaction in order to enhance the antifungal activity thereof and, as a result, found out that introduction of triiodoallyl group or iodopropargyl group to the nitrogen atom of the pyrrole ring in the said substance can much more enhance the antifungal activity thereof. Further, it has been found that derivatives of the triiodoallyl compounds and iodopropargyl compounds having a nitrogen-containing 5-membered heterocyclic ring and an antifungal activity can exert remarkable antimicrobial and antifungal activities and then the present invention has been completed upon these findings.

The compounds (I), which can be provided according to this invention, are all novel compounds and useful substances having remarkably high antifungal and antimicrobial activities.

Representative examples of the compound (I) according to this invention are recited as seen hereinbelow.

1. 1-(2',3',3'-triiodoallyl)-2,3-dichloro-4-nitropyrrole
2. 1-(2',3',3'-triiodoallyl)-2-chloro-4-nitropyrrole
3. 1-(2',3',3'-triiodoallyl)-3-nitropyrrole
4. 1-(2',3',3'-triiodoallyl)-2,3-dichloro-4-ethoxycarbonylpyrrole
5. 1-(2',3',3'-triiodoallyl)-2,3-dichloro-4-methoxycarbonylpyrrole
6. 1-(2',3',3'-triiodoallyl)-2-chloro-4-ethoxycarbonylpyrrole
7. 1-(2',3',3'-triiodoallyl)-3-ethoxycarbonylpyrrole
8. 1-(2',3',3'-triiodoallyl)-3-methoxycarbonylpyrrole
9. 1-(2',3',3'-triiodoallyl)-3-chloro-4-(3''-chloro-2''-nitrophenyl)pyrrole
10. 1-(2',3',3'-triiodoallyl)-3-(3''-chlorophenyl)pyrrole
11. 1-(2',3',3'-triiodoallyl)-3-phenylpyrrole
12. 1-(2',3',3'-triiodoallyl)-2,3,5-trichloro-4-nitropyrrole
13. 1-(2',3',3'-triiodoallyl)-2,3-dichloro-5-methoxycarbonylpyrrole
14. 1-(2',3',3'-triiodoallyl)-4-chloro-2-methoxycarbonylpyrrole
15. 1-(2',3',3'-triiodoallyl)-2-methoxycarbonylpyrrole
16. 1-(2',3',3'-triiodoallyl)-2-nitropyrrole
17. 1-(2',3',3'-triiodoallyl)imidazole
18. 1-(2',3',3'-triiodoallyl)-2-nitroimidazole
19. 1-(2',3',3'-triiodoallyl)-4-nitroimidazole
20. 2-(2',3',3'-triiodoallyl)tetrazole
21. 2-(2',3',3'-triiodoallyl)-5-methyltetrazole
22. 1-(2',3',3'-triiodoallyl)-5-methyltetrazole
23. 2-(2',3',3'-triiodoallyl)-5-phenyltetrazole
24. 2-(2',3',3'-triiodoallyl)-5-acetylaminotetrazole
25. 1-(1'-iodopropyn-3'-yl)-2,3-dichloro-4-nitropyrrole
26. 1-(1'-iodopropyn-3'-yl)-2-chloro-4-nitropyrrole
27. 1-(1'-iodopropyn-3'-yl)-3-nitropyrrole
28. 1-(1'-iodopropyn-3'-yl)-2,3,5-trichloro-4-nitropyrrole
29. 1-(1'-iodopropyn-3'-yl)-2,3-dibromo-4-nitropyrrole
30. 1-(1'-iodopropyn-3'-yl)-2,3-dichloro-4-ethoxycarbonylpyrrole
31. 1-(1'-iodopropyn-3'-yl)-3-ethoxycarbonylpyrrole
32. 1-(1'-iodopropyn-3'-yl)-3-chloro-4-(3''-chloro-2''-nitrophenyl)pyrrole
33. 1-(1'-iodopropyn-3'-yl)-3-phenylpyrrole
34. 1-(1'-iodopropyn-3'-yl)-2,3-dichloro-5-methoxycarbonylpyrrole
35. 1-(1'-iodopropyn-3'-yl)-2-methoxycarbonylpyrrole
36. 1-(1'-iodopropyn-3'-yl)-2-nitropyrrole
37. 1-(1'-iodopropyn-3'-yl)imidazole
38. 1-(1'-iodopropyn-3'-yl)-2-nitroimidazole
39. 1-(1'-iodopropyn-3'-yl)-4-nitroimidazole
40. 1-(1'-iodopropyn-3'-yl)pyrazole
41. 1-(1'-iodopropyn-3'-yl)-1,2,4-triazole
42. 1-(1'-iodopropyn-3'-yl)tetrazole
43. 2-(1'-iodopropyn-3'-yl)tetrazole
44. 1-(2',3',3'-triiodoallyl)tetrazole The novel compound (I) according to this invention can be prepared, as illustrated by the following reaction schema, by reacting an unsubstituted or substituted nitrogen-containing heterocyclic compound (II) with a reactive derivative of a 2,3,3-triiodoallyl alcohol (III) or a reactive derivative of a 3-iodopropargyl alcohol (IV) in the presence of a base in an inert organic solvent.

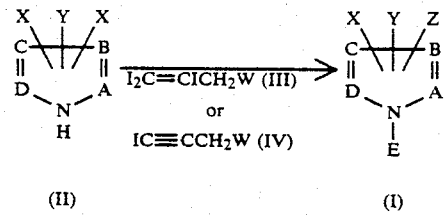

In the schema, A, B, C, D, E, X, Y and Z are as defined above and W is a hydroxy group esterified with sulfonic acid or a halogen atom.

Of the starting materials which may be employed in the present invention, triiodoallyl alcohol and iodopropargyl alcohol are well-known compounds and can be prepared by any of known methods, for example, the process as disclosed in Japanese Patent Publication No. 2444/1974. Other starting allyl or propargyl halides or allyl or propargyl esters may be prepared, for example, by reacting triiodoallyl alcohol or iodopropargyl alcohol with a halogenating agent, e.g. thionyl chloride or thionyl bromide to form the corresponding halides or by reaction of the said alcohol with an esterifying agent, e.g. toluenesulfonyl chloride, benzenesulfonyl chloride or methanesulfonic acid anhydride to form the corresponding esters.

Of another starting material (II) which may be employed in this invention, 2,3-dichloro-4-nitropyrrole (pyrrolomycin A) and 3-chloro-4-(3'-chloro-2'-nitrophenyl)pyrrole (pyrrolnitrin) are well-known as fermentative products by microbes, 3-nitropyrrole and 2,3-dichloro-4-ethoxycarbonylpyrrole may be synthesized by the processes disclosed in Tetrahedron, 22, 57 (1966) and Canadian Journal of Chemistry, 50,3223 (1972) respectively. Other starting materials may be prepared by those skilled in the art with application of the processes for preparing the aforesaid materials.

On the other hand, pyrazole, triazole, tetrazole, 5-methyltetrazole, 5-phenyltetrazole and the like are publicly known and commercially available, while 5-acetylaminotetrazole may be readily prepared by acetylation of 5-aminotetrazole.

According to the process of this invention, the heterocyclic compound (I) can be prepared by dissolving or dispersing the nitrogen-containing aromatic compound (III) in an inert organic solvent and adding a base and the triiodoallyl or iodopropyne compound (IV) to conduct N-alkylation reaction for introducing a triiodoallyl or iodopropargyl group onto the ring nitrogen atom in the said nitrogen-containing aromatic compound.

As examples of the inert organic solvent which may be employed in this invention, there may be mentioned, for example, benzene, dioxane, dichloromethane, N,N-dimethylformamide and the like.

As examples of the base which may be employed in the present reaction, there may be mentioned, for example, an inorganic base such as an alkali hydroxide, an alkali carbonate and the like and an organic base such as pyridine, triethylamine and the like.

The reaction may proceed rapidly at room temperature wherein an alkali hydroxide is employed, but may be effected under cooling, preferably at a temperature of 0° C. to 5° C., for preventing side reactions; alternatively, the reaction may be effected by heating to 40° C. to 60° C. with an organic base.

After completion of the reaction, the desired heterocyclic compound (I) may be easily isolated from the reaction mixture by a conventional method, for example, by precipitation with an inert solvent such as water and the like or extraction with an organic solvent such as toluene, ethyl acetate and the like or, if necessary, in combination with a well-known purification method such as a column chromatography over silica gel or recrystallization from an organic solvent.

This invention will be more fully illustrated by way of the following Examples and Preparation Examples.

The Examples 1 to 20 illustrate the synthesis of the new heterocyclic compound (I) according to this invention.

EXAMPLE 1

1-(2',3',3'-Triiodoallyl)-2,3-dichloro-4-nitropyrrole

To a solution of 220 mg (1.2 mmoles) of 2,3-dichloro-4-nitropyrrole (pyrrolomycin A) in 10 ml of dry N,N-dimethylformamide were added 606 ml (1 mmole) of 2,3,3-triiodoallyl-p-toluenesulfonate and 0.14 ml (1 mmole) of triethylamine and the resulting mixture was heated at 60° C. for 30 minutes. After cooling, 20 ml of cold water were added dropwise with stirring to the reaction mixture and stirring was continued for a further one hour. The so separated crystalline substance, 1-(2',3',3'-triiodoallyl)-2,3-dichloro-4-nitropyrrole, was recovered by filtration, washed with water and then dried. Yield 567 mg (95%), mp 126°–127° C.

Analysis for $C_7H_3N_2O_2Cl_2I_3$ (%): Calc'd: C, 14.04; H, 0.51; N, 4.68; Cl, 11.84; I, 63.59. Found: C, 14.34; H, 0.53; N, 4.61; Cl plus I, 76.15. Mass spectrum: $M^+$ 598.

EXAMPLE 2

1-(2',3',3'-Triiodoallyl)-3-nitropyrrole

To a solution of 112 mg (1 mmole) of 3-nitropyrrole in 5.0 ml of dry N,N-dimethylformamide were added 606 mg of 2,3,3-triiodoallyl-p-toluenesulfonate and 60 mg (1.5 mmoles) of powdery sodium hydroxide and the reaction was carried out with stirring for 15 minutes.

To the reaction mixture were added 50 ml of ethyl acetate and 50 ml of water, extraction was effected and the ethyl acetate layer was separated. The layer was washed with water, dried and concentrated under reduced pressure. To the residue were added 2.5 ml of methanol and the so separated crystalline substance, 1-(2',3',3'-triiodoallyl)-3-nitropyrrole, was recovered by filtration. Yield 306 mg (56%), mp 107°–109° C.

Analysis for $C_7H_5N_2O_2I_3$ (%): Calc'd: C, 15.86; H, 0.95; N, 5.29; I, 71.85. Found: C, 15.85; H, 0.85; N, 5.14; I, 71.82.

EXAMPLE 3

1-(2',3',3'-Triiodoallyl)-2,3-dichloro-4-ethoxycarbonylpyrrole

To a solution of 104 mg (0.5 mmoles) of 2,3-dichloro-4-ethoxycarbonylpyrrole in 5 ml of dry N,N-dimethylformamide were added 303 mg (0.5 mmoles) of 2,3,3-triiodoallyl-p-toluenesulfonate and 0.07 ml (0.5 mmoles) of triethylamine and the resulting mixture was heated at 60° C. for 2 hours. The reaction mixture was cooled, 10 ml of cold water were added with stirring thereto and the so separated crystalline substance, 1-(2',3',3'-triiodoallyl)-2,3-dichloro-4-ethyoxycarbonylpyrrole, was recovered by filtration, washed with water and then dried. Yield 281 mg (90%), mp 117°–119° C.

Analysis for $C_{10}H_8NO_2Cl_3I_3$ (%): Calc'd: C, 19.19; H, 1.29; N, 2.24; Cl, 11.33; I, 60.84. Found: C, 19.23; H, 1.24; N, 2.25; Cl plus I, 71.97.

EXAMPLE 4

1-(2',3',3'-Triiodoallyl)-3-chloro-4-(3''-chloro-2''-nitrophenyl)pyrrole

To a solution of 128 mg (0.5 mmoles) of 3-chloro-4-(3'-chloro-2'-nitrophenyl)pyrrole in 5 ml of dry N,N-dimethylformamide were added 303 mg (0.5 mmoles) of 2,3,3-triiodoallyl-p-toluenesulfonate and 24 mg (0.6 mmoles) of powdery sodium hydroxide and the resulting mixture was reacted at 25° C. for one hour. The reaction mixture was extracted with 30 ml of ethyl acetate and 30 ml of water and the ethyl acetate layer was separated. The acetate layer was washed with water, dried, and concentrated under reduced pressure. The resulting residue was purified by a silica gel chromatography (solvent system; benzene) to give 222 mg (60% yield) of 1-(2′,3′,3′-triiodoallyl)-3-chloro-4-(3″-chloro-2″-nitrophenyl)pyrrole.

Analysis for $C_{13}H_7N_2O_2Cl_3I_3$ (%): Calc'd: C, 23.15; H, 1.05; N, 4.15. Found: C, 23.51; H, 1.08; N, 4.45.

EXAMPLE 5

1-(2′,3′,3′-Triiodoallyl)-2-methoxycarbonylpyrrole

To a solution of 125 mg (1 mmole) of methyl pyrrole-2-carboxylate in 5 ml of dry N,N-dimethylformamide were added 590 mg (1 mmole) of 2,3,3-triiodoallyl-p-toluenesulfonate and 50 mg (1.2 mmoles) of powdery sodium hydroxide while cooling at 10° C. and the resulting mixture was stirred for one hour. The reaction mixture was extracted with ethyl acetate and water, the ethyl acetate layer was separated, washed with water and then dried. The ethyl acetate layer was concentrated under reduced pressure, the residual oily substance was allowed to stand with 1.0 ml of methanol, thereby separating a crystalline substance, 1-(2′,3′,3′-triiodoallyl)-2-methoxycarbonylpyrrole. It was then recovered by filtration. Yield 127 mg (23% yield), mp 88°–90° C.

Analysis for $C_9H_8NO_2I_3$ (%): Calc'd: C, 19.91; H, 1.41; N, 2.58; I, 70.13. Found: C, 19.69; H, 1.50; N, 2.77; I, 69.96.

EXAMPLE 6

1-(2′,3′,3′-Triiodoallyl)imidazole

To a solution of 340 mg (5 mmoles) of imidazole in 5.0 ml of dry DMF were added 606 mg (1 mmole) of 3-p-toluenesulfonyloxy-1,1,2-triiodo-1-propene and the reaction was effected at 25° C. for 2 hours. The reaction mixture was poured into 20 ml of ice-water while stirring vigorously and the mixture was allowed to stand for a further one hour. The crystalline substance thus separated was recovered by filtration, washed with water and then dried. Yield 440 mg (96%), mp 127°–128° C. (with decomposition).

Analysis for $C_6H_5N_2I_3$ (%): Calc'd: C, 14.83; H, 1.04; N, 5.77, I, 78.36. Found: C, 15.11; H, 1.00; N, 5.49; I, 78.13.

EXAMPLE 7

1-(2′,3′,3′-Triiodoallyl)-2-nitroimidazole

To a solution of 57 mg (0.5 mmoles) of 2-nitroimidazole and 300 mg (0.5 mmoles) of 3-p-toluenesulfonyloxy-1,1,2-triiodo-1-propene in 30 ml of dry DMF was added 0.07 ml (0.05 mmoles) of triethylamine and the resulting mixture was heated at 60° C. for one hour. After cooling, the reaction mixture was poured into 10 ml of ice-water, the brown crystalline substance thus separated was recovered by filtration, washed with water and then dried. Yield 246 mg (92%), mp 156°–158° C. (with decomposition).

Analysis for $C_6H_4N_3O_2I_3$ (%): Calc'd: C, 13.58; H, 0.76; N, 7.91; I, 71.71. Found: C, 13.26; H, 0.71; N, 7.45; I, 73.76.

EXAMPLE 8

2-(2′,3′,3′-Triiodoallyl)tetrazole and 1-(2′,3′,3′-triiodoallyl)tetrazole

To a solution of 420 mg (6 mmoles) of tetrazole in 20 ml of N,N-dimethylformamide were added 280 mg of powdery sodium hydroxide and the resulting mixture was well stirred at 20°–25° C. to form a homogeneous solution.

To the solution were added 2.95 g (5 mmoles) of 2,3,3-triiodoallyl-p-toluenesulfonic acid ester and the reaction was effected at 20°–25° C. for 3 hours. The reaction mixture was extracted with ethyl acetate and water and the ethyl acetate layer was washed with water, dried and concentrated under reduced pressure to give a pale yellow crude product. The crude product was a mixture of the two substances showing Rf values of 0.75 and 0.31, respectively, by a silica gel thin layer chromatography (solvent system:benzene-ethyl acetate=7:1). The mixture was separated and purified by a column chromatography using 75 g of silica gel (solvent system:benzene-ethyl acetate=7:1) to afford 873 mg of 2-(2′,3′,3′-triiodoallyl)tetrazole crystal from fractions showing Rf value of 0.75. Yield 35.8%, mp 92°–93° C.

Analysis for $C_4H_3N_4I_3$ (%): Calc'd: C, 9.84; H, 0.62; N, 11.49; I, 78.04. Found: C, 11.15; H, 1.03; N, 11.33; I, 77.63.

PMR spectrum (δ, CDCl₃) 5.63 ppm (—CH₂—), 8.53 ppm (tetrazole CH).

On the other hand, 1.38 g of 1-(2′,3′,3′-triiodoallyl)tetrazole crystal were given from fractions showing Rf value of 0.31. Yield 56.4%, mp 118°–119.5° C.

Analysis for $C_4H_3N_4I_3$ (%): Calc'd: C, 9.84; H, 0.62; N, 11.49; I, 78.04. Found: C, 10.34; H, 0.64; N, 11.41; I, 79.04.

PMR spectrum (δ, CDCl₃) 5.40 ppm (—CH₂—), 8.67 ppm (tetrazole CH).

EXAMPLE 9

2-(2′,3′,3′-Triiodoallyl)-5-methyltetrazole and 1-(2′,3′,3′-triiodoallyl)-5-methyltetrazole To a solution of 252 mg (3 mmoles) of 5-methyltetrazole in 15 ml of N,N-dimethylformamide were added 132 mg of powdery sodium hydroxide and the mixture was stirred for 2 hours. Then 1.77 g (3 mmoles) of 2,3,3-triiodoallyl-p-toluenesulfonic acid ester were added thereto and reaction was effected overnight at 20°–25° C. The reaction mixture was extracted with water and ethyl acetate, the ethyl acetate layer was washed with water, dried and then concentrated under reduced pressure to give a pale yellow crude product. The crude product was a mixture of the two substances showing Rf values of 0.63 and 0.16, respectively, by a silica gel chromatography (solvent system:benzene-ethyl acetate=7:1). The mixture was separated and purified by a column chromatography using 100 g of silica gel (solvent system:benzene-ethyl acetate=7:1) to give 380 mg of 2-(2′,3′,3′-triiodoallyl)-5-methyltetrazole from fractions showing Rf value of 0.63. Yield 25.0%, mp 111° C.

Analysis for $C_5H_5N_4I_3$ (%): Calc'd: C, 11.97; H, 1.00; N, 11.16; I, 75.86. Found: C, 12.12; H, 1.02; N, 11.26; I, 75.10.

PMR spectrum (δ, CDCl₃) 2.55 ppm (—CH₃), 5.50 ppm (—CH₂—).

On the other hand, 510 mg of 1-(2′,3′,3′-triiodoallyl)-5-methyltetrazole was given from fractions showing Rf value of 0.16. Yield 33.7%, mp 162°–167° C.

Analysis for $C_5H_5N_4I_3$ (%): Calc'd: C, 11.97; H, 1.00; N, 11.16; I, 75.86. Found: C, 12.01; H, 0.99; N, 11.27; I, 75.42.

PMR spectrum (δ, CDCl₃) 2.57 ppm (—CH₃), 5.20 ppm (—CH₂—).

EXAMPLE 10

2-(2',3',3'-Triiodoallyl)-5-phenyltetrazole

To a solution of 146 mg (1 mmole) of 5-phenyltetrazole in 10 ml of N,N-dimethylformamide were added 48 mg of powdery sodium hydroxide and the resulting mixture was well stirred at 20°–25° C. Then, 590 mg (1 mmole) of 2,3,3-triiodoallyl-p-toluenesulfonic acid ester were added thereto and stirring was continued overnight. To the mixture were added 10 ml of water, the so separated precipitate was recovered by filtration and dried to afford 520 mg of 2-(2',3',3'-triiodoallyl)-5-phenyltetrazole. Yield 94%, mp 187.5°–188.5° C.

Analysis for $C_5H_5N_4I_3$ (%): Calc'd: C, 11.97; H, 1.00; N, 11.16; I, 67.51. Found: C, 21.50; H, 1.22; N, 10.01; I, 66.70.

PMR spectrum (δ, $CDCl_3$) 5.60 ppm (—$CH_2$—), δ7.33–8.33 (phenyl group).

EXAMPLE 11

2-(2',3',3'-Triiodoallyl)-5-acetylaminotetrazole

A mixture of 6.18 g (60 mmoles) of 5-aminotetrazole with 56.3 ml of acetic anhydride was stirred at 20°–25° C. overnight. The so separated white precipitate was recovered by filtration, washed with a small volume of ethyl acetate and dried to give 3.5 g of 5-acetylaminotetrazole (Yield 45.8%). Thereafter, 10 ml of N,N-dimethylformamide and 120 mg of powdery sodium hydroxide were added to 571 mg (4.5 mmoles) of 5-acetylaminotetrazole and the resulting mixture was stirred at 20°–25° C. for one hour. Then, 1.77 g (3 mmoles) of 2,3,3-triiodoallyl-p-toluenesulfonic acid ester were added thereto and stirring was continued for 5 hours. To the reaction mixture was added water, the so separated white crystal was recovered by filtration, washed with a small volume of water and dried to give 578 mg of 5-acetylamino-1-(2',3',3'-triiodoallyl)tetrazole.

Yield 35.3%, mp 178°–185° C.

Analysis for $C_6H_6N_5OI_3$ (%): Calc'd: C, 13.22; H, 1.11; N, 12.86. Found: C, 12.91; H, 1.09; N, 12.47.

EXAMPLE 12

1-(1'-Iodopropyn-3'-yl)-2,3-dichloro-4-nitropyrrole

To a solution of 181 mg (1 mmole) of 2,3-dichloro-4-nitropyrrole (pyrrolomycin A) in 10 ml of dry N,N-dimethylformamide were added 340 mg (1 mmole) of p-toluenesulfonic acid ester of iodopropargyl alcohol and 50 mg of powdery sodium hydroxide and the resulting mixture was stirred at 0°–5° C. for one hour. The reaction mixture was extracted with 30 ml of water and 50 ml of benzene, the benzene layer was separated and washed twice with water. The benzene layer was dried, concentrated under reduced pressure and the residue was treated with a small valume of methanol. The so separated 1-(1'-iodopropyn-3'-yl)-2,3-dichloro-4-nitropyrrole crystal was recovered by filtration. Yield 198 mg (58%), mp 128°–131° C.

Analysis for $C_7H_3N_2O_2Cl_2I$ (%): Calc'd: C, 24.35; H, 0.88; N, 8.12; Cl, 20.56; I, 36.79. Found: C, 24.48; H, 0.83; N, 7.95; Cl plus I, 57.78.

EXAMPLE 13

1-(1'-Iodopropyn-3'-yl)-3-nitropyrrole

To a solution of 224 mg (2 mmoles) of 3-nitropyrrole in 5 ml of dry N,N-dimethylformamide were added 0.67 g (2 mmoles) of p-toluenesulfonic acid ester of iodopargyl alcohol and 100 mg of powdery sodium hydroxide and the resulting mixture was stirred at 10°–5° C. for one hour. The reaction mixture was extracted with each 50 ml portion of ethyl acetate and water and the ethyl acetate layer was separated, washed with water and dried. The ethyl acetate layer was concentrated under reduced pressure, to the residue were added 1.5 ml of methanol and the so separated 1-(1'-iodopropyn-3'-yl)-3-nitropyrrole crystal was recovered by filtration. Yield 236 mg (43%), mp 138°–140° C.

Analysis for $C_3H_5N_2O_2I$ (%): Calc'd: C, 30.47; H, 1.83; N, 10.14; I, 45.97. Found: C, 31.31; H, 1.89; N, 10.06; I, 45.34.

EXAMPLE 14

1-(1'-Iodopropyn-3'-yl)-3-chloro-4-(3''-chloro-2''-nitrophenyl)pyrrole

A solution of 130 mg of 3-chloro-4-(3'-chloro-2'-nitrophenyl)pyrrole(pyrrolnitrin) in 5 ml of dry N,N-dimethylformamide was cooled to 0°–5° C. Then, 168 mg of p-toluenesulfonic acid ester of iodopropargyl alcohol and 24 mg of powdery sodium hydroxide were added thereto and the resulting mixture was stirred for one hour and then poured into 10 ml of ice-water. The whole mixture was extracted with 20 ml of a mixture of benzene with ethyl acetate, the organic layer was washed with water, dried and concentrated under reduced pressure to leave a dark brown solid. To the residue was added 1 ml of methanol and the so separated 1-(1'-iodopropyn-3'-yl)-3-chloro-4-(3''-chloro-2''-nitrophenyl)pyrrole crystal was recovered by filtration. Yield 97 mg (46%), mp 126°–128° C.

Analysis for $C_{13}H_7N_2O_2Cl_2I_2$ (%): Calc'd: C, 37.09; H, 1.08; N, 6.65; Cl, 16.84; I, 30.14. Found: C, 38.34; H, 1.76; N, 6.83; Cl plus I, 45.73.

EXAMPLE 15

1-(1'-Iodopropyn-3'-yl)-2-carbomethoxypyrrole

To a solution of 125 mg (1 mmole) of 2-carbomethoxypyrrole in 5 ml of dry N,N-dimethylformamide were added 340 mg (1 mmole) of p-toluenesulfonic acid ester of iodopropargyl alcohol and then 46 mg of powdery sodium hydroxide were added thereto with vigorous stirring. The reaction was effected at room temperature for 20 minutes. The reaction mixture was partitioned into ethyl acetate and water, the ethyl acetate layer was separated, washed twice with a saturated aqueous solution of sodium chloride and then dried. The ethyl acetate layer was concentrated, the residual dark oily substance was purified on a silica gel TLC plate to give crystalline 1-(1'-iodopropyn-3'-yl)-2-carbomethoxypyrrole. Yield 149 mg (51%).

Analysis for $C_9H_8NO_2I$ (%): Calc'd: C, 37.39; H, 2.79; N, 4.85; I, 42.90. Found: C, 38.01; H, 2.99; N, 4.67; I, 42.90.

IR spectrum 2180 $cm^{-1}$ (—C≡C—), 1685 $cm^{-1}$ (—COO—).

EXAMPLE 16

1-(1'-Iodopropyn-3'-yl)-2-nitropyrrole

To a solution of 1.12 g (10 mmoles) of 2-nitropyrrole in 20 ml of N,N-dimethylformamide was added 0.45 g (11 mmoles) of powdery sodium hydroxide and thorough stirring gave a solution. To the solution under ice cooling were added 3.36 g (10 mmoles) of p-toluenesulfonic acid ester of iodopropargyl alcohol and the reaction was conducted under ice cooling for one hour and then at room temperature for further 15 hours. To the reaction mixture were added 30 ml of ice-water and the so separated 1-(1'-iodopropyn-3'-yl)-2-nitropyrrole crystal was recovered by filtration, washed with water and then dried. Yield 2.28 g (82%)

The crude crystal thus obtained was recrystallized from methanol to give a pure crystal of mp 102°–104° C.

Analysis for $C_7H_5N_2O_2I$ (%) Calc'd: C, 30.46; H, 1.83; N, 10.14; I, 45.97. Found: C, 30.40; H, 1.81; N, 9.99; I, 44.52.

EXAMPLE 17

1-(1'-Iodopropyn-3'-yl)pyrazole

To a solution of 136 mg (2 mmoles) of pyrazole in 5 ml of N,N-dimethylformamide were added 90 mg of powdery sodium hydroxide, the resulting mixture was well stirred at 20°–25° C. and then ice-cooled. 0.67 g (2 mmoles) of p-toluenesulfonic acid ester of iodopropargyl alcohol was added thereto, the resulting mixture was stirred for 2 hours and allowed to stand at 25° C. overnight. The reaction mixture was extracted with ethyl acetate and water, the ethyl acetate layer was washed with water, dried and then concentrated under reduced pressure to leave a crystalline substance. It was purified by a silica gel chromatography (solvent system:benzene-ethyl acetate=10:1) to afford 330 mg of 1-(1'-iodopropyn-3'-yl)pyrazole crystal. mp 94°–95° C.

Analysis for $C_6H_5N_2I$ (%): Calc'd: C, 31.03; H, 2.16; N, 12.60. Found: C, 31.73; H, 2.20; N, 12.61.

EXAMPLE 18

1-(3'-Iodopropyn-3'-yl)imidazole

To a solution of 680 mg (10 mmoles) of imidazole in 10 ml of dry DMF were added 640 mg of 3-p-toluenesulfonyloxy-1-iodopropyne and the reaction was effected at 25° C. for 2 hours. The reaction mixture was poured into 30 ml of ice-water and then extracted with 50 ml of ethyl acetate. The ethyl acetate layer was separated, washed with water and dried. The ethyl acetate layer was concentrated under reduced pressure to leave a crystalline substance, which was then washed with a small volume of ethyl acetate and dried. Yield 112 mg (24%), mp 111°–113° C. (with decomposition)

Analysis for $C_6H_5N_2I$ (%): Calc'd: C, 31.06; H, 2.17; N, 12.07; I, 54.70. Found: C, 31.19; H, 2.17; N, 11.21; I, 54.33.

EXAMPLE 19

1-(1'-Iodopropyn-3'-yl)-1,2,4-triazole

To 160 mg (2.3 mmoles) of 1,2,4-triazole were added 3 ml of N,N-dimethylformamide and 90 mg of powdery sodium hydroxide and the resulting mixture was stirred at 20°–25° C. for one hour and then ice-cooled. To the reaction mixture was added 0.67 g (2 mmoles) of p-toluenesulfonic acid ester of iodopropargyl alcohol and a temperature of the mixture was gradually allowed to raise up to room temperature while stirring over 4 hours. To the reaction mixture were added 20 ml of water and the mixture was extracted twice with 20 ml portion of ethyl acetate. Combined ethyl acetate extracts were washed twice with a saturated aqueous solution of sodium chloride and dried. The ethyl acetate extract was concentrated under reduced pressure and the residual crystalline substance was washed with a small volume of a mixture of water with methanol to give 1-(1'-iodopropyn-3'-yl)-1,2,4-triazole crystal. Yield 263 mg (56%), mp 126°–128° C.

Analysis for $C_5H_4N_3I$ (%): Calc'd: C, 25.77; H, 1.73; N, 18.03. Found: C, 25.87; H, 1.73; N, 18.33.

EXAMPLE 20

1-(1'-Iodopropyn-3'-yl)tetrazole and 2-(1'-iodopropyn-3'-yl)tetrazole

To a solution of 160 mg (2 mmoles) of tetrazole in 5 ml of N,N-dimethylformamide were added 90 mg of powdery sodium hydroxide and the mixture was stirred and then ice-cooled. 0.67 g (2 mmoles) of p-toluenesulfonic acid ester of iodopropargyl alcohol was added thereto, the reaction mixture was reacted under ice-cooling for 4 hours and then allowed to stand at 20°–25° C. overnight. To the reaction mixture were added 20 ml of water and the mixture was extracted twice with 20 ml portions of ethyl acetate. Combined ethyl acetate extracts were washed with water, dried and then concentrated under reduced pressure to leave a colorless crude product. The crude product was found to be a mixture of the two substances showing Rf values of 0.74 and 0.34, respectively, by a silica gel thin layer chromatography (solvent system:benzene-ethyl acetate=4:1). This mixture was separated and purified by a column chromatography using 50 g of silica gel (solvent system:benzene-ethyl acetate=5:1) and 183 mg of 2-(1'-iodopropyn-3'-yl)tetrazole crystal were obtained from fractions showing Rf value of 0.74. Yield 39%, mp 92°–95° C.

Analysis for $C_4H_3N_4I$ (%): Calc'd: C, 20.53; H, 1.29; N, 23.94. Found: C, 20.27; H, 1.30; N, 23.88.

PMR spectrum (δ, CDCl$_3$) 5.50 ppm (—CH$_2$—), 8.45 ppm (tetrazole CH).

On the other hand, 258 mg of 1-(1'-iodopropyn-3'-yl)tetrazole crystal were obtained from fractions with Rf value of 0.34. Yield 55%, mp 92°–95° C.

Analysis for $C_4H_3N_4I$ (%): Calc'd: C, 20.53; H, 1.29; N, 23.94. Found: C, 20.62; H, 1.26; N, 23.96.

PMR spectrum (δ, CDCl$_3$) 5.30 ppm (—CH$_2$—), 8.66 ppm (tetrazole CH).

The novel heterocyclic compound (I) of this invention is a low-toxic substance and useful as antibacterial and antifungal agents. In particular, the present compound can exert a growth inhibition activity against a wide variety of fungi and hence is useful for prophylaxis and improvement in undesirable conditions caused by growth of fungi. More specifically, the present compound can be employed, for medicinal purposes, for prevention and treatment of various infectious diseases caused by fungi, sterilization of instruments and machines, maintenance of aseptic environment and the like. Further, the present compound may be employed, as agricultural and industrial antifungals and preservatives in order to maintain nature and quality of agricultural and industrial products, such as seed, woods and wooden products, paper industrial art products, leathers, fiber products and the like and also as active ingredients for antifungal paints.

More illustratively, the present compound may be incorporated into a solution or ointment as an active ingredient at a ratio of 0.1–5%, preferably 0.5–2%, for medicinal purposes as a treating agent for external diseases caused by those fungi, typically, belonging to, e.g. the genera of Candida, Aspergillus, Trichophyton, Cryptococcus and so on and can accomplish treatment purposes by applying to the diseased parts. Moreover, the present compound may be employed as active ingredients for disinfectants of machines and instruments and others for the purposes of preventing growth of pathogenic bacteria and fungi and maintaining aseptic environment as medicinal uses.

The present compound (I) is also useful in agricultural and industrial fields. Especially, it is said in these fields that a serious damage would be caused to product value with development of saprogenous bacill or fungi in agricultural and industrial products such as seed, seedlings, woods, wooden products, paper industrial art products, leathers, adhesives, paints, synthetic resins and the like as well as their manufacture environment such as water for industrial use and the like. The present compound shows a growth inhibiting activity against harmful bacteria and fungi in agricultural and industrial fields and, accordingly, can be applied for maintaining nature and quality of products and environmental conditions in these fields.

In agricultural and industrial fields, the present compound may be usually applied in the form of a preparation having the compound supported on a conventional carrier, for example, an oil-soluble liquid, an emulsifiable concentrate, a paste, a dust, a wettable powder, an aerosol, an antifungal paint and the like. As the carrier which may be employed in this invention, there may be mentioned for instance, an inorganic solid carrier such as clay, talc, bentonite, kaolin, silicic anhydride, calcium carbonate and the like; an organic solvent type carrier such as tyrosine, ligroin, xylene, DMF, DMSO and the like; and a gaseous carrier such as dimethyl ether, fureon gas and the like.

As the auxiliary agents which may enhance a preparation property in this invention, there may be mentioned, for instance, an ionic or non-ionic surface active agent and a polymeric compound such as vinyl acetate, methyl cellulose and the like, and there may be also employed other antifungals or preservatives such as thiabendazole and the like or insecticides such as chlordane and the like in combination with the present compound.

In practical application, a content of the present compound in the preparation may vary depending upon the form of a preparation, but it is generally suitable to be 0.01–95% by weight, preferably 0.2–10% by weight.

The preparation examples of agricultural and industrial antibacterial and antifungal compositions are given hereinbelow. In the following examples, all parts are by weight unless otherwise indicated.

I. WETTABLE POWDERS

Preparation Example 1

Fourty parts of 1-(2',3',3'-triiodoallyl)-2,3-dichloro-4-nitropyrrole, 5 parts of polyoxyethylene alkyl aryl ether, 3 parts of lignin sulfonic acid and 52 parts of diatomaceous earth were uniformly pulverized and admixed to give a wettable powder containing 40% of the active ingredient.

Preparation Example 2

Fourty parts of 1-(2',3',3'-triiodoallyl)imidazole, 5 parts of polyoxyethylene alkyl aryl ether, 3 parts of lignin sulfonic acid and 52 parts of diatomaceous earth were uniformly pulverized and admixed to give a wettable powder containing 40% of the active ingredient.

Preparation Example 3

Fourty parts of 1-(1'-iodopropyn-3'-yl)-2,3-dichloro-4-nitropyrrole, 5 parts of polyoxyethylene alkyl aryl ether, 3 parts of lignin sulfonic acid and 52 parts of diatomaceous earth to give a wettable powder containing 40% of the active ingredient.

Preparation Example 4

Fourty parts of 1-(1'-iodopropyn-3'-yl)pyrazole, 5 parts of polyoxyethylene alkyl aryl ether, 3 parts of lignin sulfonic acid and 52 parts of diatomaceous earth to give a wettable powder containing 40% of the active ingredient.

Preparation Example 5

Fourty parts of 2-(2',3',3'-triiodoallyl)tetrazole, 5 parts of polyoxyethylene alkyl aryl ether, 3 parts of lignin sulfonic acid and 52 parts of diatomaceous earth were uniformly pulverized and admixed to give a wettable powder containing 40% of the active ingredient.

II. GRANULES

Preparation Example 1

Twelve parts of 1-(2',3',3'-triiodoallyl)-2,3-dichloro-4-nitropyrrole, 1 part of calcium lignin sulfonate, 30 parts of bentonite and 57 parts of clay were uniformly pulverized and admixed and the resulting mixture was kneaded with a suitable volume of water, granulated and dried to give a granule containing 12% of the active ingredient.

Preparation Example 2

Twelve parts of 1-(2',3',3'-triiodoallyl)-2,3-dichloro-4-nitropyrrole, 1 part of calcium lignin sulfonate, 30 parts of bentonite and 57 parts of clay were uniformly pulverized and admixed and the resulting mixture was kneaded with a suitable volume of water, granulated and dried to give a granule containing 12% of the active ingredient.

Preparation Example 3

Twelve parts of 1-(1'-iodopropyn-3'-yl)-2,3-dichloro-4-nitropyrrole, 1 part of calcium lignin sulfonate, 30 parts of bentonite and 57 parts of clay were uniformly pulverized and admixed and the resulting mixture was kneaded with a suitable volume of water, granulated and dried to give a granule containing 12% of the active ingredient.

Preparation Example 4

Twelve parts of 1-(1'-iodopropyn-3'-yl)-1,2,4-triazole, 1 part of calcium lignin sulfonate, 30 parts of bentonite and 57 parts of clay were uniformly pulverized and admixed and the resulting mixture was kneaded with a suitable volume of water, granulated and dried to give a granule containing 12% of the active ingredient.

Preparation Example 5

Twelve parts of 1-(2',3',3'-triiodoallyl)tetrazole, 1 part of calcium lignin sulfonate, 30 parts of bentonite and 57 parts of clay were uniformly pulverized and admixed and the resulting mixture was kneaded with a suitable volume of water, granulated and dried to give a granule containing 12% of the active ingredient.

III. EMULSIFIABLE CONCENTRATES

Preparation Example 1

Twenty parts of 1-(2',3',3'-triiodoallyl)-3-nitropyrrole, 30 parts of N,N-dimethylformamide, 35 parts of xylene and 15 parts of polyoxyethylene alkyl aryl ether were uniformly admixed to give an emulsifiable concentrate containing 20% of the active ingredient.

Preparation Example 2

Twenty parts of 1-(2',3',3'-triiodoallyl)imidazole, 30 parts of N,N-dimethylformamide, 35 parts of xylene and 15 parts of polyoxyethylene alkyl aryl ether were uniformly admixed to give an emulsifiable concentrate containing 20% of the active ingredient.

Preparation Example 3

Twenty parts of 1-(1'-iodopropyn-3'-yl)-3-nitropyrrole, 30 parts of N,N-dimethylformamide, 35 parts of xylene and 15 parts of polyoxyethylene alkyl aryl ether were uniformly admixed to give an emulsifiable concentrate containing 20% of the active ingredient.

Preparation Example 4

Twenty parts of 1-(1'-iodopropyn-3'-yl)tetrazole, 30 parts of N,N-dimethylformamide, 35 parts of xylene and 15 parts of polyoxyethylene alkyl aryl ether were uniformly admixed to give an emulsifiable concentrate containing 20% of the active ingredient.

Preparation Example 5

Twenty parts of 2-(2',3',3'-triiodoallyl)-5-methyltetrazole, 30 parts of N,N-dimethylformamide, 35 parts of xylene and 15 parts of polyoxyethylene alkyl aryl ether were uniformly admixed to give an emulsifiable concentrate containing 20% of the active ingredient.

IV. DUSTS

Preparation Example 1

Three parts of 1-(2',3',3'-triiodoallyl)-2,3-dichloro-4-nitropyrrole, 0.5 part of silicic acid anhydride fine powder, 0.5 part of calcium stearate, 50 parts of clay and 46 parts of talc were uniformly pulverized and admixed to give a dust containing 3% of the active ingredient.

Preparation Example 2

Three parts of 1-(2',3',3'-triiodoallyl)imidazole, 0.5 part of silicic acid anhydride fine powder, 0.5 part of calcium stearate, 50 parts of clay and 46 parts of talc were uniformly pulverized and admixed to give a dust containing 3% of the active ingredient.

Preparation Example 3

Three parts of 1-(2',3',3'-triiodoallyl)-5-methyltetrazole, 0.5 parts of silicic acid anhydride fine powder, 0.5 part of calcium stearate, 50 parts of clay and 46 parts of talc were uniformly pulverized and admixed to give a dust containing 3% of the active ingredient.

Preparation Example 4

Three parts of 1-(1'-iodopropyn-3'-yl)-2,3-dichloro-4-nitropyrrole, 0.5 part of silicic acid anhydride fine powder, 0.5 part of calcium stearate, 50 parts of clay and 46 parts of talc were uniformly pulverized and admixed to give a dust containing 3% of the active ingredient.

Preparation Example 5

Three parts of 2-(1'-iodopropyn-3'-yl)tetrazole, 0.5 part of silicic acid anhydride fine powder, 0.5 part of calcium stearate, 50 parts of clay and 46 parts of talc were uniformly admixed to give a dust containing 3% of the active ingredient.

Then useful activities of the present compound (I) are illustrated hereinbelow by means of acute toxicity data (Table 1), antifungal activity data (Tables 2, 3, 4 and 5) and experimental data on treatment of trichophytosis in guinea pigs.

TABLE 1

| Dosage (mg/kg) | 1-(2',3',3'-triiodoallyl)-2,3-dichloro-4-nitropyrrole | 1-(2',3',3'-triiodoallyl)-3-nitropyrrole | 1-(1'-iodopropyn-3'-yl)-2,3-dichloro-4-nitropyrrole | 1-(1'-iodopropyn-3'-yl)-3-nitropyrrole |
|---|---|---|---|---|
| | Acute Toxicity (mouse, p.o.) | | | |
| 100 | All animals survived | All animals survived | — | — |
| 200 | All animals survived | All animals survived | All animals survived | All animals survived |
| 500 | — | — | All animals survived | All animals survived |
| 800 | All animals survived | All animals survived | All animals survived | All animals survived |

TABLE 2

Antibacterial Activity (in medicinal field)

| Test organism | Minimal Inhibitory Conc. (MIC) (γ/ml) | |
|---|---|---|
| | 1-(2',3',3'-triiodoallyl)-2,3-dichloro-4-nitropyrrole | 1-(2',3',3'-triiodoallyl)-2-chloro-4-nitropyrrole |
| Staphylococcus aureus 209P JC-1 | 31.2 | 6.25 |
| Staphylococcus epidermidis ATCC 14990 | 31.2 | 6.25 |
| Staphylococcus faecalis ATCC 8043 | 31.2 | 6.25 |
| Bacillus anthracis No. 109 | 31.2 | 6.25 |
| Bacillus anthracis No. 119 | — | — |
| Escherichia coli NIHJ JC-2 | 12.5 | 12.5 |
| Citrobacter freundii GN-346 | 12.5 | 12.5 |
| Salmonella typhi O-901-W | 12.5 | 12.5 |
| Shigella sonnei EW 33 Type I | 6.25 | 12.5 |
| Klebsiella pneumoniae PCI-602 | 25 | 25 |
| Proteus vulgaris OX-19 | 6.25 | 12.5 |
| Serratia marcescens MB-3848 | 6.25 | 12.5 |
| Pseudomonas cepacia M-0527 | 6.25 | 12.5 |
| Pseudomonas maltophilia M-0627 | — | — |
| | 1-(2',3',3'-triiodoallyl)-imidazole | 1-(2',3',3'-triiodoallyl)-2-nitroimidazole |
| Staphylococcus aureus 209P JC-1 | 12.5 | 12.5 |
| Staphylococcus epidermidis ATCC 14990 | 12.5 | 12.5 |
| Staphylococcus faecalis ATCC 8043 | 25 | 25 |
| Bacillus anthracis No. 109 | 12.5 | 6.25 |

TABLE 2-continued

Antibacterial Activity (in medicinal field)

| Test organism | Minimal Inhibitory Conc. (MIC) (γ/ml) | |
|---|---|---|
| Bacillus anthracis No. 119 | — | — |
| Escherichia coli NIHJ JC-2 | 12.5 | 25 |
| Citrobacter freundii GN-346 | 12.5 | 3.12 |
| Salmonella typhi O-901-W | 12.5 | 12.5 |
| Shigella sonnei EW 33 Type I | 6.5 | 3.12 |
| Klebsiella pneumoniae PCI-602 | 12.5 | 6.25 |
| Proteus vulgaris OX-19 | 12.5 | 6.25 |
| Serratia marcescens MB-3848 | 12.5 | 25 |
| Pseudomonas cepacia M-0527 | 6.25 | 3.12 |
| Pseudomonas maltophilia M-0627 | — | — |
| | 2-(2',3',3'-triiodoallyl)-tetrazole | 1-(2',3',3'-triiodoallyl)tetrazole |
| Staphylococcus aureus 209P JC-1 | 6.25 | 31.3 |
| Staphylococcus epidermidis ATCC 14990 | — | — |
| Staphylococcus faecalis ATCC 8043 | — | — |
| Bacillus anthracis No. 109 | — | — |
| Bacillus anthracis No. 119 | 1.56 | 0.78 |
| Escherichia coli NIHJ JC-2 | 12.5 | 3.13 |
| Citrobacter freundii GN-346 | — | — |
| Salmonella typhi O-901-W | 6.25 | 1.56 |
| Shigella sonnei EW 33 Type I | 6.25 | 3.13 |
| Klebsiella pneumoniae PCI-602 | 12.5 | 3.13 |
| Proteus vulgaris OX-19 | 12.5 | 6.25 |
| Serratia marcescens MB-3848 | 6.25 | 3.13 |
| Pseudomonas cepacia M-0527 | 1.56 | 0.78 |
| Pseudomonas maltophilia M-0627 | 1.56 | 0.78 |

TABLE 3

Antifungal Activity (in Medicinal Field) Minimal Inhibitory Conc. (MIC) (γ/ml)

| Test compound | Candida alubicans GA-24 | Cryptococcus neoformans Cr-1 | Trichophyton metagrophytes 530324 | Trichophyton interdigitale | Aspergillus fumigatus Saito |
|---|---|---|---|---|---|
| 1-(2',3',3'-triiodoallyl)-2,3-dichloro-4-nitropyrrole | 0.39 | 0.19 | 0.19 | 1.56 | 0.19 |
| 1-(2',3',3'-triiodoallyl)-3-nitropyrrole | 0.19 | 0.39 | 0.19 | 0.39 | 0.09 |
| 1-(2',3',3'-triiodoallyl)-imidazole | 1.56 | 6.25 | 1.56 | 3.12 | 6.25 |
| 1-(2',3',3'-triiodoallyl)-2-nitroimidazole | 0.78 | 25 | 0.78 | 1.56 | 0.78 |
| 2-(2',3',3'-triiodoallyl)-tetrazole | 0.19 | 0.78 | 0.09 | 0.09 | 0.19 |
| 1-(2',3',3'-triiodoallyl)-tetrazole | 3.12 | 3.12 | 0.39 | 0.39 | 0.78 |
| 2-(2',3',3'-triiodoallyl)-5-methyltetrazole | 0.78 | 1.56 | 0.19 | 0.19 | 0.19 |
| 1-(2',3',3'-triiodoallyl)-5-methyltetrazole | 3.12 | 6.25 | 0.78 | 0.78 | 0.78 |
| 2-(2',3',3'-triiodoallyl)-5-phenyltetrazole | 12.5 | 12.5 | 1.56 | 3.12 | 6.25 |
| 2-(2',3',3'-triiodoallyl)-5-acetylaminotetrazole | 100 | 100 | 3.12 | 3.12 | 12.5 |
| 1-(1'-iodopropyn-3'-yl)-2,3-dichloro-4-nitropyrrole | 0.78 | 1.56 | 0.09 | 0.39 | 0.39 |
| 1-(1'-iodopropyn-3'-yl)-3-nitropyrrole | 0.78 | 0.09 | 0.19 | 0.78 | 0.09 |
| 1-(1'-iodopropyn-3'-yl)pyrazole | 3.12 | 0.78 | 0.39 | 0.39 | 0.78 |
| 1-(1'-iodopropyn- | 3.12 | 0.78 | 1.56 | 0.78 | 0.78 |

TABLE 3-continued

Antifungal Activity (in Medicinal Field)
Minimal Inhibitory Conc. (MIC) (γ/ml)

| Test compound | Candida alubicans GA-24 | Cryptococcus neoformans Cr-1 | Trichophyton metagrophytes 530324 | Trichophyton interdigitale | Aspergillus fumigatus Saito |
|---|---|---|---|---|---|
| 3'-yl)-1,2,4-triazole | | | | | |
| 1-(1'-iodopropyn-3'-yl)-tetrazole | 1.56 | 0.39 | 0.78 | 0.78 | 0.39 |
| 2-(1'-iodopropyn-3'-yl)-tetrazole | 3.12 | 0.78 | 1.56 | 1.56 | 1.56 |

TABLE 4

Antifungal Activity (in Industrial Field)
Minimal Inhibitory Conc. (MIC) (γ/ml)

| Test organism | 1-(2',3',3'-triiodoallyl)-2,3-dichloro-4-nitropyrrole | 1-(2',3',3'-triiodoallyl)-2-chloro-4-nitropyrrole |
|---|---|---|
| Aspergillus flavus ATCC 6275 | 0.78 | 0.39 |
| Aspergillus terreus PQMD 82 j | 1.56 | 1.56 |
| Penicillium luteum ATCC 9644 | 6.25 | 1.56 |
| Mucor spinescens IAM Mu3 | >50 | 3.13 |
| Cladosporium herbarum IAM F-517 | 0.20 | 0.20 |
| Pullularia pullulans IAM F-24 | >50 | 1.56 |
| Trichoderma T-1 ATCC 9645 | 6.25 | 6.25 |
| Chaetomium globosum ATCC 6205 | 50 | 3.13 |
| Aspergillus fumigatus IAM 2621 | 25 | 0.78 |
| Rhizopus nigricans S.N. 32 | — | — |

| Test organism | 1-(2',3',3'-triiodoallyl)-imidazole | 1-(2',3',3'-triiodoallyl)-2-nitroimidazole |
|---|---|---|
| Aspergillus flavus ATCC 6275 | 3.13 | 1.56 |
| Aspergillus terreus PQMD 82 j | 0.78 | 0.78 |
| Penicillium luteum ATCC 9644 | 0.78 | 3.13 |
| Mucor spinescens IAM Mu3 | 6.25 | 6.25 |
| Cladosporium herbarum IAM F-517 | 0.39 | 0.39 |
| Pullularia pullulans IAM F-24 | 3.13 | 3.13 |
| Trichoderma T-1 ATCC 9645 | 6.25 | 6.25 |
| Chaetomium globosum ATCC 6205 | 1.56 | 1.56 |
| Aspergillus fumigatus IAM 2621 | 6.25 | 6.25 |
| Rhizopus nigricans S.N. 32 | — | — |

| Test organism | 1-(1'-iodopropyn-3'-yl)pyrazole | 1-(1'-iodopropyn-3'-yl)-1,2,4-triazole |
|---|---|---|
| Aspergillus flavus ATCC 6275 | 1.56 | 6.25 |
| Aspergillus terreus PQMD 82 j | 0.78 | 0.39 |
| Penicillium luteum ATCC 9644 | 0.78 | 3.13 |
| Mucor spinescens IAM Mu3 | 1.56 | 6.25 |
| Cladosporium herbarum IAM F-517 | 3.13 | 3.13 |
| Pullularia pullulans IAM F-24 | 3.13 | 3.13 |
| Trichoderma T-1 ATCC 9645 | 3.13 | 3.13 |
| Chaetomium globosum ATCC 6205 | 12.5 | 25 |
| Aspergillus fumigatus IAM 2621 | 1.56 | 50 |
| Rhizopus nigricans S.N. 32 | 1.56 | 3.13 |

| Test organism | 1-(1'-iodopropyn-3'-yl)tetrazole | 2-(1'-iodopropyn-3'-yl)tetrazole |
|---|---|---|
| Aspergillus flavus ATCC 6275 | 1.56 | 6.25 |
| Aspergillus terreus PQMD 82 j | 0.20 | 0.78 |
| Penicillium luteum ATCC 9644 | 1.56 | 3.13 |
| Mucor spinescens IAM Mu3 | 3.13 | 3.13 |
| Cladosporium herbarum IAM F-517 | 1.56 | 3.13 |
| Pullularia pullulans IAM F-24 | 1.56 | 6.25 |
| Trichoderma T-1 ATCC 9645 | 0.78 | 3.13 |
| Chaetomium globosum ATCC 6205 | 3.13 | 25 |
| Aspergillus fumigatus IAM 2621 | 12.5 | 25 |
| Rhizopus nigricans S.N. 32 | 3.13 | 6.25 |

| Test organism | 1-(1'-iodopropyn-3'-yl)-2,3-dichloro-4-nitropyrrole | 1-(1'-iodopropyn-3'-yl)-2-chloro-4-nitropyrrole |
|---|---|---|
| Aspergillus flavus ATCC 6275 | 0.39 | 0.39 |
| Aspergillus terreus PQMD 82 j | 0.39 | 0.19 |
| Penicillium luteum ATCC 9644 | 0.78 | 0.39 |
| Mucor spinescens IAM Mu3 | 0.39 | 0.78 |
| Cladosporium herbarum IAM F-517 | 6.25 | 1.56 |
| Pullularia pullulans IAM F-24 | 6.25 | 1.56 |
| Trichoderma T-1 ATCC 9645 | 3.12 | 3.12 |
| Chaetomium globosum ATCC 6205 | 1.56 | 12.5 |

TABLE 4-continued

Antifungal Activity (in Industrial Field)
Minimal Inhibitory Conc. (MIC) (γ/ml)

| Test organism | Test compound | |
|---|---|---|
| Aspergillus fumigatus IAM 2621 | <0.09 | 0.19 |
| Rhizopus nigricans S.N. 32 | — | — |

| | 2-(2',3',3'-triiodoallyl)-tetrazole | 2-(2',3',3'-triiodoallyl)-5-methyl-tetrazole |
|---|---|---|
| Aspergillus flavus ATCC 6275 | 0.78 | 1.56 |
| Aspergillus terreus PQMD 82 j | 0.78 | 0.39 |
| Penicillium luteum ATCC 9644 | 6.25 | 6.25 |
| Mucor spinescens IAM Mu3 | 1.56 | 1.56 |
| Cladosporium herbarum IAM F-517 | 6.25 | 6.25 |
| Pullularia pullulans IAM F-24 | 0.76 | 3.13 |
| Trichoderma T-1 ATCC 9645 | 3.13 | 6.25 |
| Chaetomium globosum ATCC 6205 | 12.5 | 6.25 |
| Aspergillus fumigatus IAM 2621 | 6.25 | 1.56 |
| Rhizopus nigricans S.N. 32 | 3.13 | 1.56 |

TABLE 5

Antibacterial and Antifungal-Activities
(in Agricultural Field)
Minimal Inhibitory Conc. (MIC) (γ/ml)

| Test organism | Test Compound | |
|---|---|---|
| | 1-(2',3',3'-triiodoallyl)-2,3-dichloro-4-nitropyrrole | 1-(2',3',3'-triiodoallyl)-3-nitropyrrole |
| Xanthomonas campestris pv. oryzae | >50 | 25 |
| Xanthomonas campestris pv. citri | >50 | 50 |
| Pseudomonas syringae pv. tabaci | >50 | 6.25 |
| Erwinia carotovora | >50 | 6.25 |
| Corynebacterium michiganense | 6.25 | 0.98 |
| Phricularia oryzae | 6.25 | 1.56 |
| Diaporithe citri | 0.78 | 0.39 |
| Colletotrichum lagenarium | 1.56 | 0.39 |
| Alternaria kikuchiana | 6.25 | 0.78 |
| Glomerella cingulata | 1.56 | 0.39 |
| Botrytis cinerea | 12.5 | 0.19 |
| Fusarium oxysporum f. lycopersici | 6.25 | 0.78 |
| Gibberella fujikuroi | 3.12 | 0.39 |
| Cochliobolus miyabeanus | 50 | 12.5 |
| Pellicularia filamentosa | >50 | 50 |

| | 1-(2',3',3'-triiodoallyl)-imidazole | 1-(2',3',3'-triiodoallyl)-2-nitroimidazole |
|---|---|---|
| Xanthomonas campestris pv. oryzae | 25 | 12.5 |
| Xanthomonas campestris pv. citri | 25 | 25 |
| Pseudomonas syringae pv. tabaci | 12.5 | 12.5 |
| Erwinia carotovora | 12.5 | 12.5 |
| Corynebacterium michiganense | 1.56 | 3.13 |
| Phricularia oryzae | 3.13 | 1.56 |
| Diaporithe citri | 0.78 | 1.56 |
| Colletotrichum lagenarium | 1.56 | 0.78 |
| Alternaria kikuchiana | 1.56 | 0.78 |
| Glomerella cingulata | 1.56 | 0.78 |
| Botrytis cinerea | 1.56 | 0.19 |
| Fusarium oxysporum f. lycopersici | 1.56 | 1.56 |
| Gibberella fujikuroi | 0.78 | 0.78 |
| Cochliobolus miyabeanus | 6.25 | 0.78 |
| Pellicularia filamentosa | 50 | 25 |

TABLE 5-continued

Antibacterial and Antifungal-Activities
(in Agricultural Field)
Minimal Inhibitory Conc. (MIC) (γ/ml)

| Test organism | Test Compound | |
|---|---|---|
| | 2-(2',3',3'-triiodoallyl)-tetrazole | 2-(2',3',3'-triiodoallyl)-5-methyl-tetrazole |
| Xanthomonas campestris pv. oryzae | 6.25 | 6.25 |
| Xanthomonas campestris pv. citri | 25 | 50 |
| Pseudomonas syringae pv. tabaci | >100 | >100 |
| Erwinia carotovora | >100 | >100 |
| Corynebacterium michiganense | 12.5 | 25 |
| Phricularia oryzae | 3.13 | 3.13 |
| Diaporithe citri | 0.78 | 0.78 |
| Colletotrichum lagenarium | 0.78 | 0.78 |
| Alternaria kikuchiana | 3.13 | 1.56 |
| Glomerella cingulata | 0.39 | 0.39 |
| Botrytis cinerea | 0.39 | 0.39 |
| Fusarium oxysporum f. lycopersici | 1.56 | 3.13 |
| Gibberella fujikuroi | 0.39 | 0.78 |
| Cochliobolus miyabeanus | 1.56 | 6.25 |
| Pellicularia filamentosa | 50 | >100 |

| | 1-(1'-iodopropyn-3'-yl)-2,3-dichloro-4-nitropyrrole | 1-(1'-iodopropyn-3'-yl)-3-nitropyrrole |
|---|---|---|
| Xanthomonas campestris pv. oryzae | 0.39 | 0.39 |
| Xanthomonas campestris pv. citri | — | — |
| Pseudomonas syringae pv. tabaci | — | — |
| Erwinia carotovora | — | — |
| Corynebacterium michiganense | — | — |
| Phricularia oryzae | — | — |
| Diaporithe citri | — | — |
| Colletotrichum lagenarium | 1.56 | 3.12 |
| Alternaria kikuchiana | 0.78 | 1.56 |
| Glomerella cingulata | 0.19 | 0.78 |
| Botrytis cinerea | 0.39 | 0.78 |
| Fusarium oxysporum f. lycopersici | 3.12 | 3.12 |
| Gibberella fujikuroi | 1.56 | 3.12 |
| Cochliobolus miyabeanus | 12.5 | 6.25 |
| Pellicularia filamentosa | >50 | 50 |

THERAPEUTIC EXPERIMENT

White Hartly-strain guinea pigs, a group consisting of 3 animals, were depilated at 4 portions of skin on back (each two at right and left, 4×6 cm) and then a suspension of Trichophyton mentagrophytes (Sabouraud's broth, live microbe number 2×10⁷/ml) was applied by brushing to each portion in each 0.5 ml volume.

After 2 days from the fungal inoculation, a preparation of the test compound as prescribed in Table 6 was applied to each one diseased part at right and left in each 0.25 ml volume once per day over 8 consecutive days.

TABLE 6

| Test preparation for therapy | |
|---|---|
| Test compound | 1.0 g |
| Diethyl sebacate | 10.0 g |
| Purified water | 10.0 g |
| Officially defined ethanol | ed. lib. |
| Total | 100 g |

The above test procedures were similarly repeated for a 1% preparation of pyrrolnitrin [3-chloro-4-(2'-nitro-3'-chlorophenyl)pyrrole] and a 1% preparation of chlotrimazol [1-(O-chloro-α,α-diphenylbenzyl)imidazole] and used as controls, together with non-treated groups.

Evaluation of effectiveness by visual observation revealed that the present compound exhibit good therapeutic results in all of thickening, redness and desquamation in the diseased skin portion, as illustrated in Table 7.

TABLE 7

| | Therapeutic Effect | | | |
|---|---|---|---|---|
| | Test compound | | | |
| Observed item | 1-(2',3',3'-triiodoallyl)-2,3-dichloro-4-nitropyrrole | 1-(2',3',3'-triiodoallyl)-3-nitropyrrole | pyrrolnitrin | chlotrimazol |
| Thickening | effective | effective | effective | effective |
| Redness | prominently effective | prominently effective | ineffective | ineffective |
| Desquamation | effective | effective | ineffective | effective |

After application over 8 days, animals were sacrificed, 3 skin slices were taken from each diseased part, and cultivated on Sabouraud's agar plate for 7 days to determine a reducing culture positive rate.

As shown in Table 8, a clear reduction in reducing culture positive rate was observed in the group treated with the present compound, as compared with the positive control group as well as the non-treated control group.

TABLE 8

| | Reducing Culture Positive Rate (%) | | | | |
|---|---|---|---|---|---|
| | Test compound | | | | |
| Day for culture | 1-(2',3',-3'-triiodoallyl)-2,3-dichloro-4-nitropyrrole | 1-(2',3'-3'-triiodoallyl)-3-nitropyrrole | pyrrolnitrin | chlotrimazol | non-treated |
| 3 days | 0 | 16.7 | 62 | 75 | 100 |
| 5 days | 16.7 | 25.0 | 87 | 96 | 100 |
| 7 days | 16.7 | 33.3 | 87 | 96 | 100 |

What is claimed is:

1. A compound having the formula

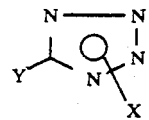

wherein
Y represents a hydrogen atom or —CH$_3$, and
X represents —CH$_2$CI=CI$_2$ or —CH$_2$C≡CI.

2. A compound according to claim 1 wherein said compound is 1-(2',3',3'-triiodoallyl)tetrazole.

3. A compound according to claim 1 wherein the compound is 2-(2',3',3'-triiodoallyl)tetrazole.

4. A compound according to claim 1 wherein said compound is 1-(1'-iodopropyn-3'-yl)tetrazole.

5. A compound according to claim 1 wherein said compound is 2-(1'-iodopropyn-3'-yl)tetrazole.

6. A compound according to claim 1 wherein said compound is 1-(2',3',3'-triiodoallyl)-5-methyltetrazole.

7. A compound according to claim 1 wherein said compound is 2-(2',3',3'-triiodoallyl)-5-methyltetrazole.

8. An antibacterial and antifungal composition which comprises as an active ingredient a compound of the formula

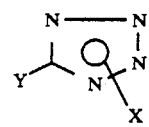

wherein
Y represents a hydrogen atom or —CH$_3$, and
X represents —CH$_2$CI=CI$_2$ or —CH$_2$C≡CI.

9. A composition according to claim 8 wherein said compound is 1-(2',3',3'-triiodoallyl)tetrazole.

10. A composition according to claim 8 wherein said compound is 2-(2',3',3'-triiodoallyl)tetrazole.

11. A composition according to claim 8 wherein said compound is 1-(1'-iodopropyn-3'-yl)tetrazole.

12. A composition according to claim 8 wherein said compound is 2-(1'iodopropyn-3'-yl)tetrazole.

13. A composition according to claim 8 wherein said compound is 1-(2',3',3'-triiodoallyl)-5-methyltetrazole.

14. A composition according to claim 8 wherein said compound is 2-(2',3',3'-triiodoallyl)-5-methyltetrazole.

* * * * *